United States Patent
Yoon et al.

(10) Patent No.: US 7,104,998 B2
(45) Date of Patent: Sep. 12, 2006

(54) HIP JOINT ROBOT SYSTEM AND ROBOT MOUNTING APPARATUS

(75) Inventors: Yong San Yoon, Daejon (KR); Jung Ju Lee, Daejon (KR); Dong Su Kwon, Daejon (KR); Ho Chul Shin, Daegu (KR); Young Bae Park, Chungcheongbuk-do (KR)

(73) Assignee: Korea Advanced Institute of Science and Technology, Daejon (KR)

( * ) Notice: Subject to any disclaimer, the term of this patent is extended or adjusted under 35 U.S.C. 154(b) by 105 days.

(21) Appl. No.: 10/178,726

(22) Filed: Jun. 25, 2002

(65) Prior Publication Data

US 2003/0004516 A1 Jan. 2, 2003

(30) Foreign Application Priority Data

Jun. 30, 2001 (KR) .......................... 2001-0038973

(51) Int. Cl.
*A61B 17/32* (2006.01)
(52) U.S. Cl. .......................................... 606/89; 606/79
(58) Field of Classification Search ................. 606/53, 606/54, 79, 80, 86, 87, 89; 83/821, 829
See application file for complete search history.

(56) References Cited

U.S. PATENT DOCUMENTS

| | | | | | |
|---|---|---|---|---|---|
| 4,257,411 | A | * | 3/1981 | Cho | 606/96 |
| 4,781,182 | A | * | 11/1988 | Purnell et al. | 606/96 |
| 4,973,331 | A | * | 11/1990 | Pursley et al. | 606/54 |
| 4,979,949 | A | * | 12/1990 | Matsen et al. | 606/53 |
| 5,019,077 | A | * | 5/1991 | De Bastiani et al. | 606/54 |
| 5,162,039 | A | * | 11/1992 | Dahners | 602/23 |
| 5,236,432 | A | * | 8/1993 | Matsen et al. | 606/88 |
| 5,299,288 | A | * | 3/1994 | Glassman et al. | 700/245 |
| 5,300,077 | A | * | 4/1994 | Howell | 606/96 |
| 5,312,409 | A | * | 5/1994 | McLaughlin et al. | 606/86 |
| 5,343,385 | A | * | 8/1994 | Joskowicz et al. | 700/57 |
| 5,546,942 | A | * | 8/1996 | Zhang | 600/427 |
| 5,578,039 | A | * | 11/1996 | Vendrely et al. | 606/88 |
| 5,611,802 | A | * | 3/1997 | Samuelson et al. | 606/86 |
| 5,616,147 | A | * | 4/1997 | Gadelius | 606/102 |

(Continued)

FOREIGN PATENT DOCUMENTS

WO WO00/00093 * 1/2000

*Primary Examiner*—Eduardo C. Robert
*Assistant Examiner*—David Comstock
(74) *Attorney, Agent, or Firm*—Morrison & Foerster LLP (57) ABSTRACT

A robot mounting apparatus for a hip joint operation robot capable of firmly attaching a hip joint operation robot to a femur in order for operation robot to perform an accurate femoral canal cavity operation, and a hip joint operation robot system using the same. The robot mounting apparatus for a hip joint operation robot, comprising: a fixing means for fixing to a femur, including: a bar having a predetermined length and being arranged in perpendicular to a femur; and a seizing means having a predetermined shape for seizing the femur, the seizing means forms at an end of the bar; an installation unit having a predetermined shaped for installing the operation robot thereon, the installation unit is positioned near an end portion of the femur; and a link having a predetermined length for connecting the installation unit and the bar of the fixing means, the link is installed in parallel with respect to a longitudinal direction of the femur. The hip joint operation robot system employs the robot mounting apparatus and the robot firmly mounted on the robot mounting apparatus.

24 Claims, 6 Drawing Sheets

U.S. PATENT DOCUMENTS

| | | | |
|---|---|---|---|
| 5,649,930 A * | 7/1997 | Kertzner | 606/96 |
| 5,704,941 A * | 1/1998 | Jacober et al. | 606/88 |
| 6,228,089 B1 * | 5/2001 | Wahrburg | 606/86 |
| 6,267,785 B1 * | 7/2001 | Masini | 623/23.22 |
| 6,514,253 B1 * | 2/2003 | Yao | 606/53 |
| 6,554,837 B1 * | 4/2003 | Hauri et al. | 606/87 |
| 6,679,888 B1 * | 1/2004 | Green et al. | 606/86 |
| 6,837,892 B1 * | 1/2005 | Shoham | 606/130 |
| 2002/0116003 A1 * | 8/2002 | Deloge et al. | 606/87 |

* cited by examiner

HIP JOINT ROBOT SYSTEM AND ROBOT MOUNTING APPARATUS

FIELD OF THE INVENTION

The present invention relates to a hip joint operation robot system, and in particular to a robot mounting apparatus for a hip joint operation robot which are capable of firmly attaching the hip joint operation robot to a femur in order for the hip joint operation robot to perform an accurate femoral canal cavity operation, and a hip joint operation robot system using the same.

BACKGROUND OF THE INVENTION

Generally, an artificial joint is formed of an acetabular portion and a femur portion. The above femur portion includes a ball engaged with the acetabular portion, a stem inserted into a human's femur and a neck for connecting the stem and the ball. Here, the acetabular portion is formed of an abrasion resistance material like a polyethylene. The femur portion is formed of a certain material like a metal or ceramic. However, the acetabular portion and the femur portion may be made of the same ceramic material.

In a joint operation, when an artificial joint which is formed of the above material and has the above structure is engaged with a human's femur having a cortical bone or a porous bone and a bone cavity therein, since the stem of the artificial joint must be properly engaged with the femur, the femur must have a longitudinal femoral canal cavity therein of which the diameter and length correspond to those of the engaged stem. The operation in which the stem of the artificial joint is engaged to the femur will be described in detail.

FIGS. 1A through 1F are views for describing a manual operation of the hip joint operation.

Figure 1A:
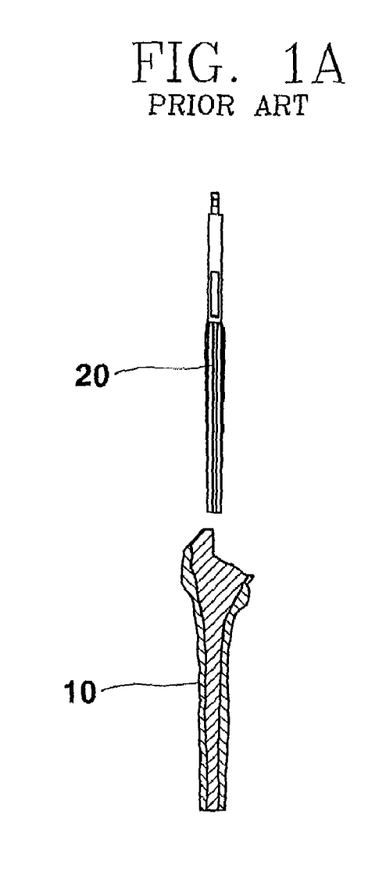
FIGS. 1A through 1F are views illustrating procedures for manually performing a hip joint operation in the prior art.
Figure 1B:
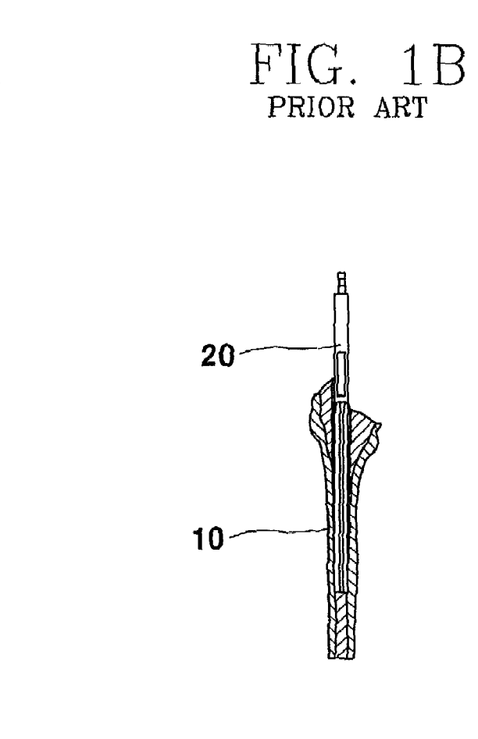
Figure 1C:
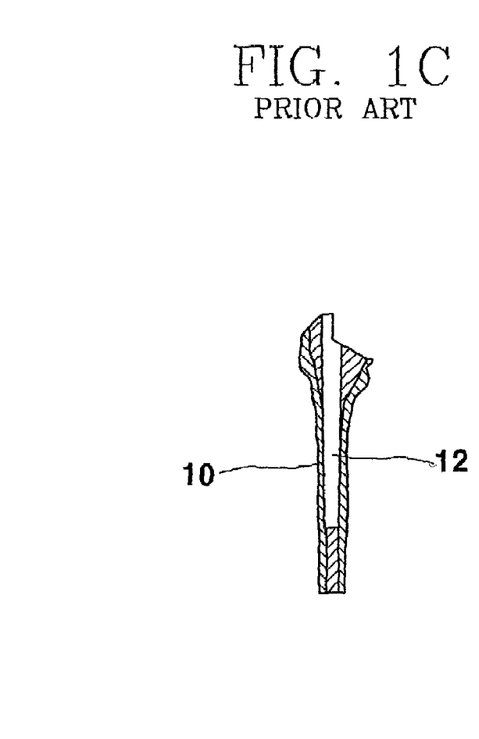

When a reamer 20 is stated to inserted into the femur 10 engaged with a hip joint, as shown in FIG. 1A, and is inserted by a certain depth in a longitudinal direction of the femur 10, as shown in FIG. 1B, and is removed from the femur 10, as shown in FIG. 1C, a reamer insertion femoral canal cavity 12 is formed in the femur 10.

Figure 1D:
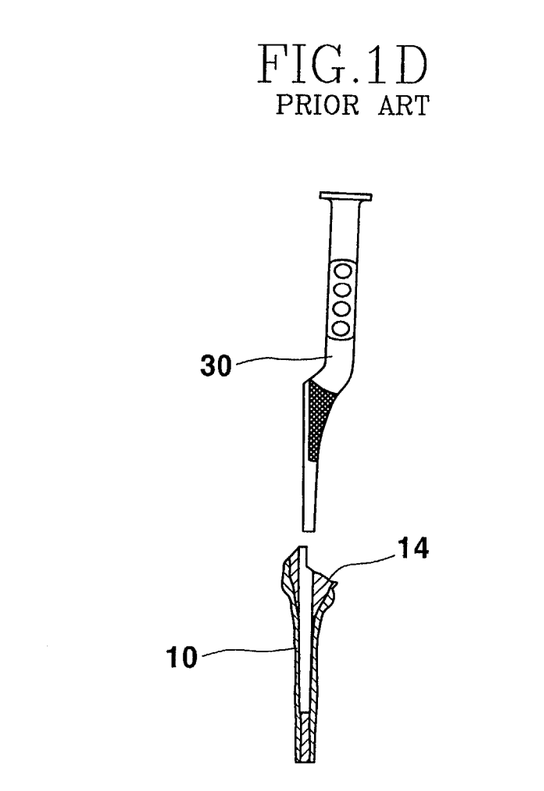
Figure 1E:
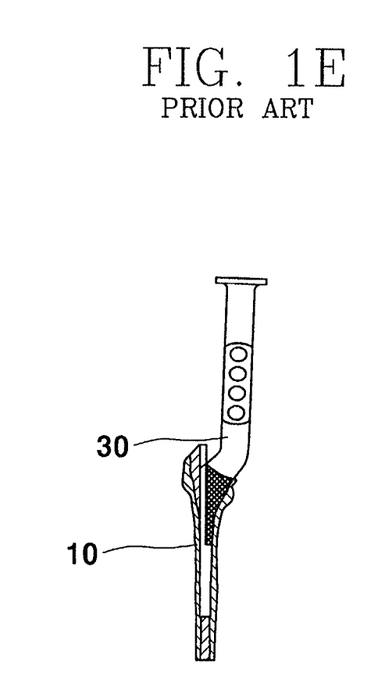
Figure 1F:
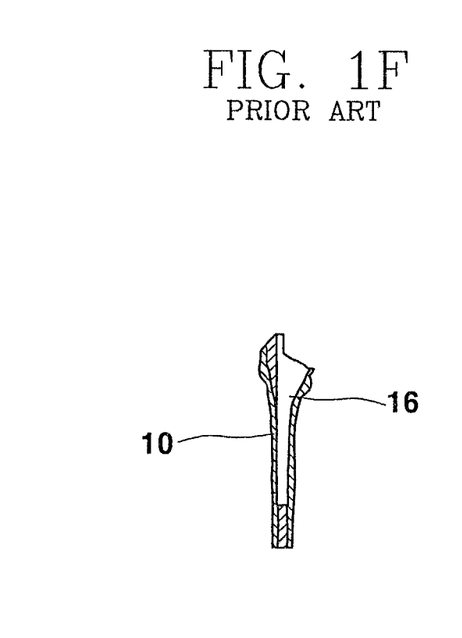

Next, as shown in FIGS. 1D through 1E, when a broach 30 having the same shape as that of an artificial joint is inserted into the reamer insertion femoral canal cavity 12, the femur 10 is excavated or formed in the same shape as the broach 30. Here, in the drawing, reference numeral 14 represents a bone removing portion formed in the femur 10 by the broach 30.

At this time, it is impossible to accurately form a femoral canal cavity in the femur by a manual operation in order for the position and size of the same to be accurately matched with those of the artificial joint. Therefore, when the artificial joint operation is manually performed, the artificial joint may not be properly or accurately engaged with the femur.

In order to improve the above problems which occur due to the manual work in which the artificial joint is engaged to the femur, a femur is machined using an operation robot. The femur operating by the robot will be described in detail with reference to the accompanying drawings.

Figure 2:
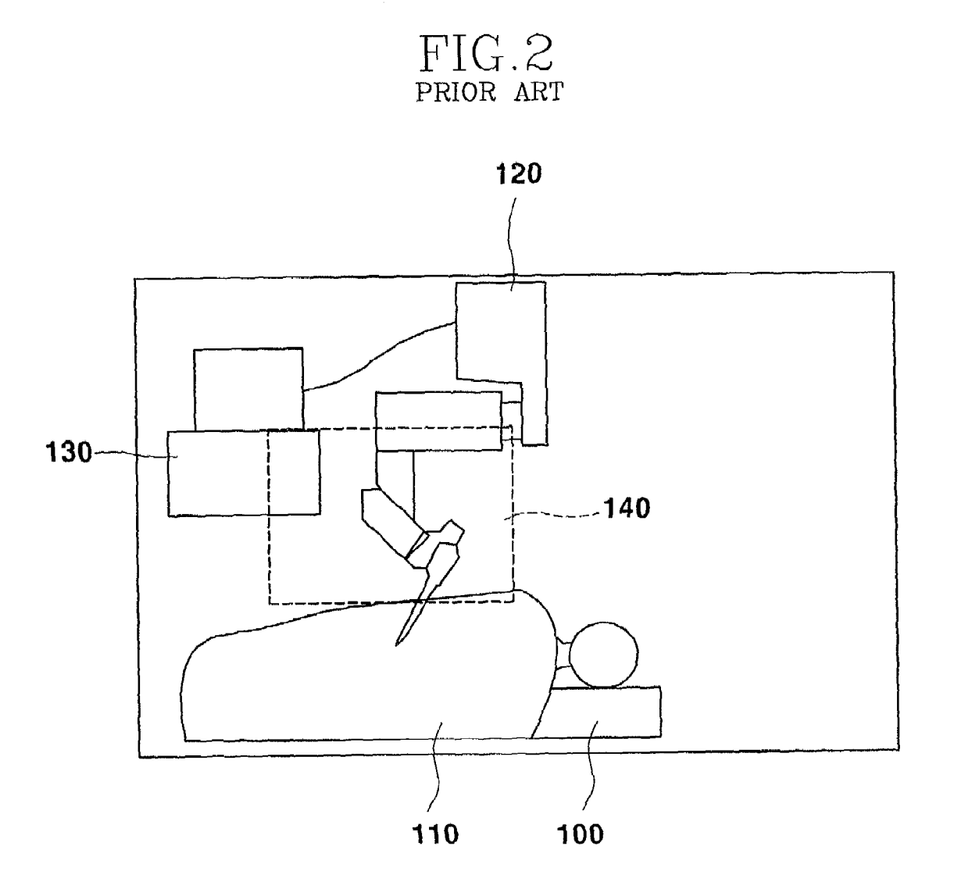
FIG. 2 is a view illustrating the construction of a prior art hip joint operation robot system.

FIG. 2 is a view illustrating a prior art robot operation system which includes an operating table 100, an operation robot 120 fixedly installed in an operating room or operating table for thereby performing an operation of a patient 110, and a computer 130 connected with the operation robot 120 for controlling an operation performed by the operation robot 120. Here, in the drawings, dotted line 140 represents a work space in which the operation robot 120 works during the operation.

In the above robot operation system, since it is possible to accurately process the shape of the femoral canal cavity to match with the shape of the artificial joint compared to the operation in which the femoral canal cavity is processed by a manual method, it is possible to accurately engage the artificial joint to the femoral canal cavity.

However, since the prior art robot operation system has a big volume and is fixedly installed in a floor of the operating room or the operating table, it cannot be moved one place to another. In addition, as indicated by the dotted line of FIG. 2, the prior art operation system has a large workspace. Also, the prior art robot system needs an additional system for detecting a position of a corresponding bone before the operation and an apparatus for preventing the femur from being moved during the operation, thereby the prior art robot operation system is expensive and is not widely used.

SUMMARY OF THE INVENTION

Accordingly, it is an object of the present invention to provide a robot mounting apparatus for a hip joint operation robot, which is small and capable of stably attaching the hip joint operation robot to a femur so that the hip joint operation robot performs an accurate femoral canal cavity operation, and a hip joint operation robot system using the robot mounting apparatus.

It is another object of the present invention to provide a robot mounting apparatus for a hip joint operation robot, which is small, movable and capable of stably attaching the hip joint operation robot to a femur, so that the hip joint operation robot implements an accurate operation of a femoral canal cavity, and a hip joint operation robot system using the robot mounting apparatus.

In order to achieve the above objects, there is provided a robot mounting apparatus for a hip joint operation robot, comprising: a fixing means for fixing to a femur, including: a bar having a predetermined length and being arranged in perpendicular to a femur; and a seizing means having a predetermined shape for seizing the femur, the seizing means forms at an end of the bar; an installation unit having a predetermined shape for installing the operation robot thereon, the installation is positioned near an end portion of the femur; and a link having a predetermined length for connecting the installation unit and the bar of the fixing means, the link is installed in parallel with respect to a longitudinal direction of the femur.

In order to achieve the above objects, there is provided a hip joint operation robot system, comprising: a robot for performing an artificial joint operation with respect to a femur of a patient; a robot mounting apparatus for supporting the robot, one end of the robot mounting apparatus is fixed to the femur of the patient and the other end installs the robot thereon; and a computer electrically connected with the robot for controlling the robot to perform the artificial joint operation.

BRIEF DESCRIPTION OF THE DRAWINGS

The present invention will become better understood with reference to the accompanying drawings which are given only by way of illustration and thus are not limitative of the present invention, wherein.

DETAILED DESCRIPTION OF THE PREFERRED EMBODIMENTS

Figure 3:
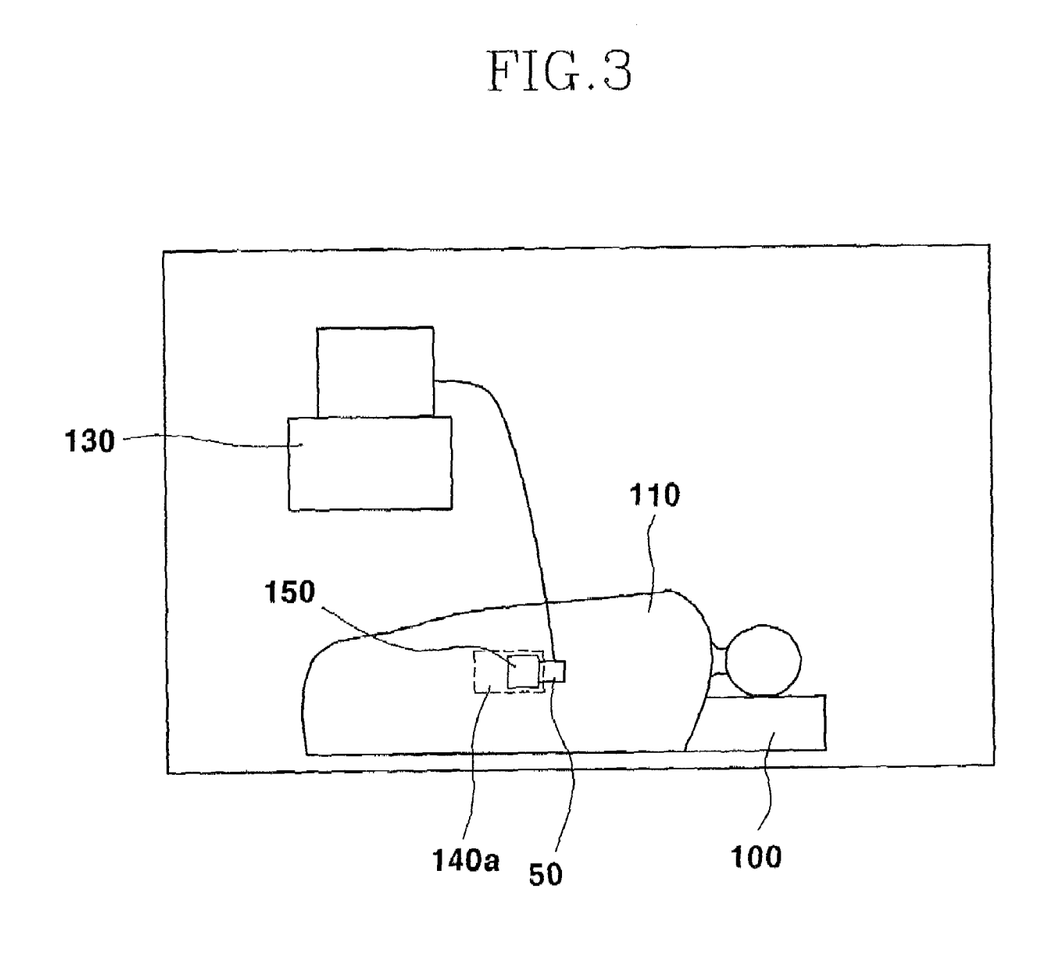
FIG. 3 is a view illustrating the construction of a hip joint operation robot system according to the present invention.

FIG. 3 is a view illustrating the construction of a hip joint operation robot system according to the present invention. The hip joint operation robot system includes an operating table 100, an operation robot 50 for performing an operation with respect to a patient 110 on the operating table 100, a robot mounting apparatus 150 which is engaged to a femur of the patient 110 and stably and fixedly installs the hip joint operation robot 50 thereon so that the hip joint operating robot 50 performs accurately an artificial joint operation near a corresponding operation portion of the femur, and a computer 130 electrically connected with the robot 50 for controlling the robot 50 to perform the artificial joint operation. In the drawings, dotted line 140a represents a workspace in which the operation robot 50 reaches during the operation. In the present invention, the workspace is relatively smaller than that of the prior art robot system.

In the hip joint operation robot system, the robot mounting apparatus 150 for installing the operation robot 50 and being fixed to the femur will be described in detail with reference to the accompanying drawings.

Figure 4:
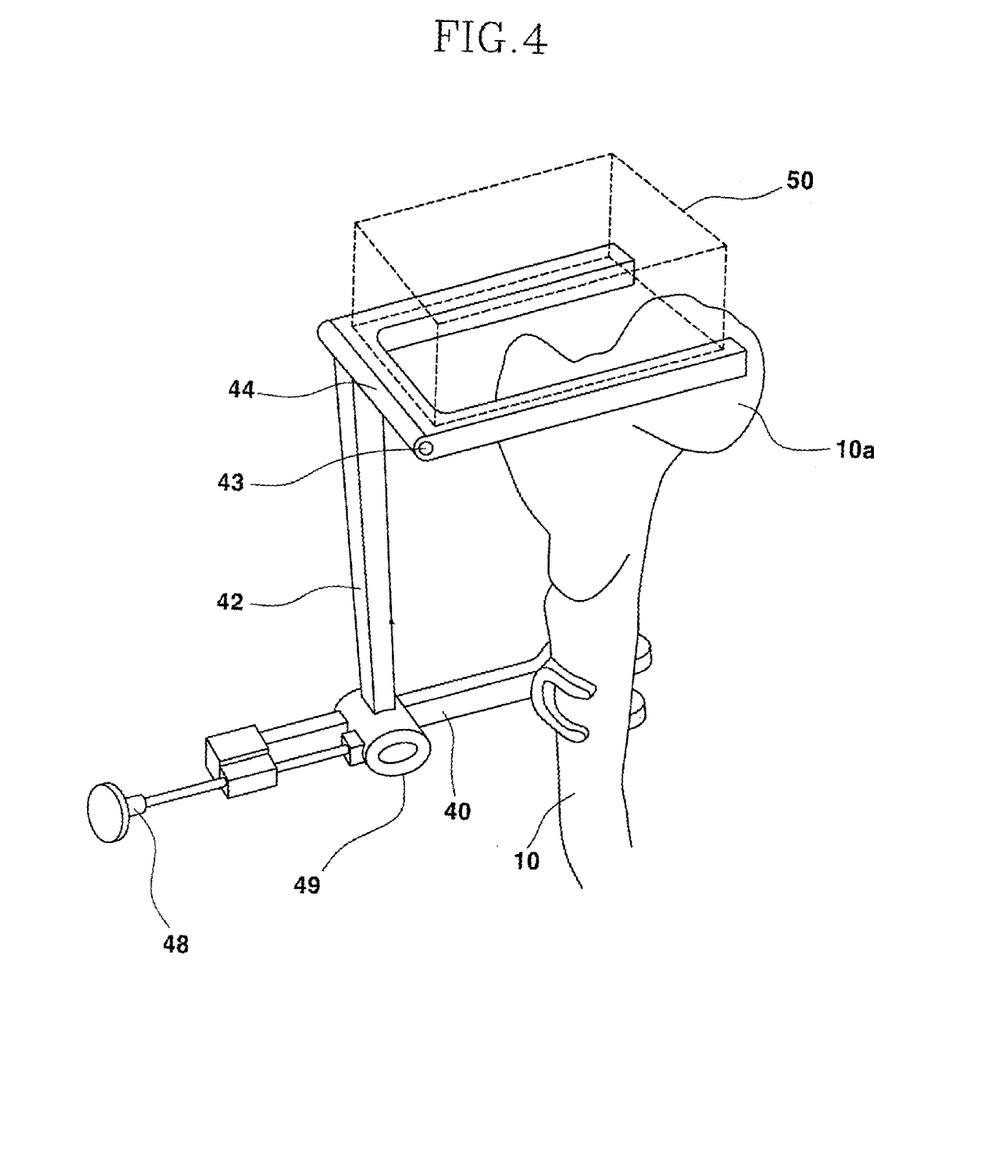
FIG. 4 is a perspective view illustrating a robot mounting apparatus for a hip joint operation robot according to the present invention.
Figure 5:
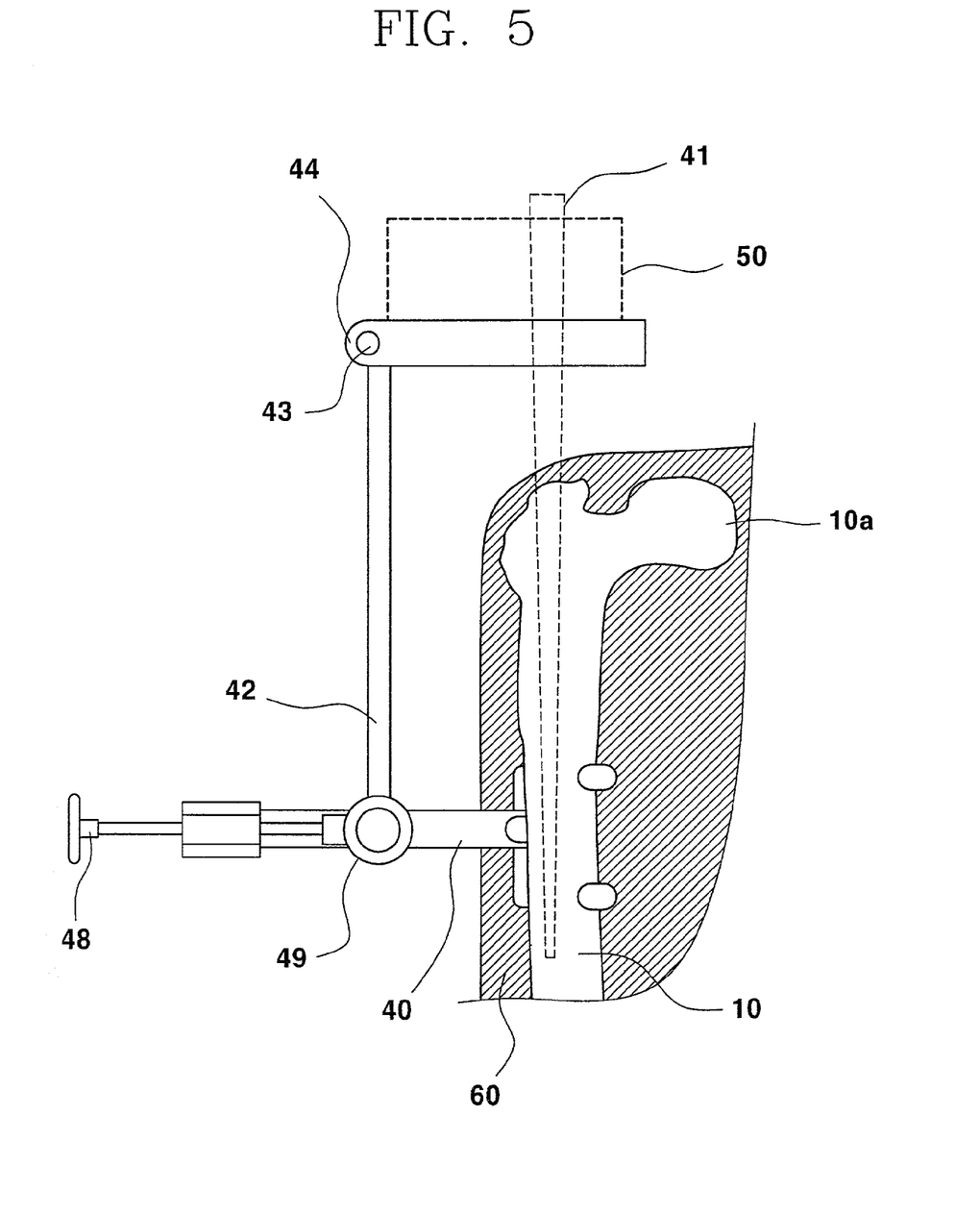
FIG. 5 is a cross-sectional view illustrating a robot mounting apparatus for a hip joint operation robot according to the present invention.

FIG. 4 is a perspective view illustrating the robot mounting apparatus for a hip joint operation robot according to the present invention, and FIG. 5 is a cross-sectional view illustrating the robot an mounting apparatus according to the present invention.

As shown therein, the robot mounting apparatus 150 for a hip joint operation robot includes a fixing clamp 40 for surrounding and clamping a femur 10, a clamp adjusting unit 48 for controlling the fixing clamp 40 so that the fixing clamp 40 stably seize the femur 10, a robot installation unit 44 which is positioned near an end portion of the femur in the side of the hip joint and installs the operation robot 50 thereon, and a link 42 which has an end connected with the robot installation unit 44 by a first engaging member 43, and the other end connected with the fixing clamp 40 by a second engaging member 49.

As shown in FIG. 5, the robot installation unit 44 is constructed in such a manner that the operation robot 50 is fixedly installed thereon. The robot installation unit 44 is formed like a Korean character, 'ㄷ', which is read as 'Digeut', or a bracket shape '[', so that the operation robot 50 performs an operation in a stable state.

In addition, the fixing clamp 40 and the robot installation unit 44 are assembled at a predetermined angle with respect to the link 42. At this time, the installation angle of the same may be adjusted and then fixed. The first and second engaging members 43 and 49 are fixing the link 42, the fixing clamp 40 and the robot installation unit 44, like a engaging manner such as a ball+slider engagement, a slider+ slider engagement, a ball+socket engagement, or hinge+ hinge engagement.

Therefore, the robot installation unit 44 can be engaged with the femur 10 at various angles, so that the operation robot 50 performs an operation of the femur 10 of the patient at the optimum angle. Namely, when the link and/or fixing clamp and/or the robot installation unit are adjusted with predetermined angles each other with respect to corresponding engaging members therebetween, the corresponding engagement members fixed the link and/or fixing clamp and/or the robot installation unit to each other in order to maintain the predetermined angle.

In the preferred embodiment of the present invention, the robot installation unit 44 installs the operation robot 50 thereon and then fixes the same using a predetermined engaging unit (not shown). We can easily appreciate that the robot installation unit 44 may be integrally formed with the operation robot as one integrated body as another preferred embodiment of the present invention. Namely, since a measurement reamer position must be measured with respect to the robot before the operation robot 50 performs an operation, the robot installation unit 44 installs the operation robot which may be separatably fixed. However, if an apparatus is used for measuring the position of the measurement reamer position with respect to the robot, the robot installation unit may be integrally formed with the operation robot as one integrated body.

Also, even though, the robot installation unit 44 is formed like a Korean character, 'ㄷ', which is read as 'Digeut', or a bracket shape '[' in the preferred embodiment of the present invention, so that the operation robot 50 performs an operation in a stable state, we can easily appreciate that the robot installation unit may be formed in a certain shape such as a plate shape or modified shape therefrom.

In the preferred embodiments of the present invention, even though the fixing clamp 40 is a Roman clamp, we can easily appreciate that a fixing apparatus having a seizing unit at its one end may be adapted like an adhesive, screw, and other elements having the same function. In addition, the fixing clamp 40 may further include a certain engaging unit (not shown) capable of moving and fixing the link 42 thereon.

In addition, the robot mounting apparatus for a hip joint operation robot according to the present invention has a dimension of 15 cm each in horizontal, vertical and height sides, and the hip joint operation robot system using the robot mounting apparatus has a dimension of 15 cm each in horizontal, vertical and height sides. Therefore, the volume of the hip joint operation robot system is relatively smaller than that of the prior art operation robot system.

The artificial joint operation using the robot mounting apparatus for a hip joint operation robot and a hip joint operation robot system using the same according to the present invention will be described.

First of all, in order to start an artificial joint operation, a surgical doctor cuts a tissue 60 of a patient's leg and pelvis and slightly pulls out a femur. Next, the fixing clamp 40 stably attaches to the femur 10. At this time, since the fixing clamp 40 is installed inside the tissue 60, the fixing clamp 40 is not exposed to the outside of the femur 10. Thereafter, the robot installation unit 44 is installed. At this time, the distance, direction and angle between the robot installation unit 44 and the femur 10 are freely and optimally adjusted by the link 42 and the engaging member 43.

After the robot installation unit 44 is installed, the measurement reamer 41 is inserted into the bone cavity of the femur bone 10, and a relative position between the measurement reamer 41 and the robot installation unit 44 is measured, and then the measurement reamer 41 is removed. Thereafter, the robot is stably and fixedly installed on the robot installation unit. At this time, the relative position with respect to the femur of the operation robot is not changed irrespective of the movement of the femur. When the operation robot is installed based on the above method, in a state that the position of the operation robot is in a stable state, a femoral canal cavity which is accurately matched with the size and diameter of the artificial joint which will be inserted thereinto, is formed in the femur.

Next, the artificial joint is inserted into the femoral canal cavity which is accurately formed in the femur, so that the artificial joint is accurately fixed at a desired position.

As described above, since the robot mounting apparatus for a hip joint operation robot according to the present invention has a small and simple structure and is capable of stably fixing the position of the operation robot with respect to an operating portion, the operating robot performs the operation accurately.

In addition, the robot mounting apparatus for a hip joint operation robot according to the present invention is fixed only to the femur, not to a certain portion of the system such as the operating table or a floor of the operation room, the operation robot system is movable, and the volume of the same is significantly decreased. In addition, since the operation robot performs an operation in a relatively decreased space with respect to the operating portion of the patient, it is possible to decrease the workspace of the robot system. Furthermore, the operation robot accurately performs the operation irrespective of the movement of the femur while the operation robot performs an operation.

The hip joint operation robot system using the robot mounting apparatus for a hip joint operation robot according to the present invention is stably fixed with respect to the femur, so that it is possible to accurately perform an operation of the femur irrespective of the movement of the femur and performs an operation in a relatively decreased space compared to the conventional art.

As the present invention may be embodied in several forms without departing from the spirit or essential characteristics thereof, it should also be understood that the above-described examples are not limited by any of the details of the foregoing description, unless otherwise specified, but rather should be construed broadly within its spirit and scope as defined in the appended claims, and therefore all changes and modifications that fall within the meets and bounds of the claims, or equivalences of such meets and bounds are therefore intended to be embraced by the appended claims.

What is claimed is:

1. A robot mounting apparatus, comprising:
    a fixing clamp for fixing to a femur, comprising a bar having a predetermined length and positioned substantially perpendicular to a longitudinal direction of the femur; and a seizing unit having a predetermined shape for seizing the femur, wherein the seizing unit is located at an end of the bar;
    a hip joint installation unit having a predetermined shape, a hip joint operation robot installed on the hip joint installation unit, wherein the hip joint installation unit is positioned near an end portion of the femur; and
    a link having a predetermined length for connecting the hip joint installation unit and the bar of the fixing clamp, wherein the link is positioned substantially parallel with respect to the longitudinal direction of the femur,
    wherein the robot mounting apparatus is capable of being positioned near an end portion of the femur in the side of the hip joint and adapted to engage at various angles such that the hip joint operation robot operates on the femur for hip implant surgery,
    further wherein the hip joint operation robot is capable of forming a femoral canal cavity in the femur that matches a size of an artificial hip joint stem.

2. The apparatus of claim 1, wherein said fixing clamp is a Roman clamp.

3. The apparatus of claim 1, wherein said seizing unit comprises an adhesive or screw.

4. The apparatus of claim 1, wherein said hip joint installation unit has a predetermined thickness and is formed like a Korean character, 'ㄷ', which is read as 'Digeut', or a bracket shape '['.

5. The apparatus of claim 1, wherein said hip joint installation unit and the link are fixed by a first engaging member with a predetermined angle therebetween, the hip joint installation unit and the link are relatively rotatable with respect to the first engaging member.

6. The apparatus of claim 5, wherein said first engaging member comprises a ball and slider engagement, a slider and slider engagement, a ball and socket engagement or hinge and hinge engagement.

7. The apparatus of claim 5, wherein said fixing clamp and the link are fixed by a second engaging member with a predetermined angle therebetween, the hip joint installation unit and the link are relatively rotatable with respect to the first engaging member.

8. The apparatus of claim 7, wherein said second engaging member comprises a ball and slider engagement, a slider and slider engagement, a ball and socket engagement or hinge and hinge engagement.

9. The apparatus of claim 1, wherein said fixing clamp and the link are fixed by a third engaging member with a predetermined angle therebetween, the hip joint installation unit and the link are relatively rotatable with respect to the first engaging member.

10. The apparatus of claim 9, wherein said third engaging member comprises a ball and slider engagement, a slider and slider engagement, a ball and socket engagement or hinge and hinge engagement.

11. The apparatus of claim 1, wherein said fixing clamp further includes an adjusting means for controlling the seizing unit to stably seize the femur.

12. The apparatus of claim 1, wherein said fixing clamp further includes an engaging means for adjusting the link to move along the bar of the fixing clamp and fixing the same to the bar at a predetermined position of the bar.

13. A hip joint operation robot system, comprising:
    a robot that performs an artificial joint operation with respect to a femur;
    a robot mounting apparatus for supporting the robot, wherein one end of the robot mounting apparatus is fixed to the femur and the robot is installed at the other end of the robot mounting apparatus; and
    a computer electrically connected with the robot for controlling the robot to perform the artificial joint operation, wherein said robot mounting apparatus comprises:
    a fixing clamp for fixing to a femur, comprising a bar having a predetermined length and positioned substantially perpendicular to a longitudinal direction of the femur; and a seizing unit having a predetermined shape for seizing the femur, wherein the seizing unit is located at an end of the bar;

a hip joint installation unit having a predetermined shape, a hip joint operation robot installed on the hip joint installation unit, wherein the hip joint installation unit is positioned near an end portion of the femur; and a link having a predetermined length for connecting the hip joint installation unit and the bar of the fixing clamp, wherein the link is positioned substantially parallel with respect to the longitudinal direction of the femur, wherein the robot mounting apparatus is capable of being positioned near an end portion of the femur in the side of the hip joint and adapted to engage at various angles such that the hip joint operation robot operates on the femur for hip implant surgery, further wherein the hip joint operation robot is capable of forming a femoral canal cavity in the femur that matches a size of an artificial hip joint stem.

14. The system of claim 13, wherein said hip joint installation unit has a predetermined thickness and is formed like a Korean character, 'ㄷ', which is read as 'Digeut', or a bracket shape '['.

15. The system of claim 13, wherein said robot and the hip joint installation unit are integrally formed in one body.

16. The system of claim 13, wherein said hip joint installation unit and the link are fixed by a first engaging member with a predetermined angle therebetween, the hip joint installation unit and the link are relatively rotatable with respect to the first engaging member.

17. The system of claim 16, wherein said first engaging member comprises a ball and slider engagement, a slider and slider engagement, a ball and socket engagement or hinge and hinge engagement.

18. The system of claim 16, wherein said fixing clamp and the link are fixed by a second engaging member with a predetermined angle therebetween, the hip joint installation unit and the link are relatively rotatable with respect to the first engaging member.

19. The system of claim 13, wherein said second engaging member comprises a ball and slider engagement, a slider and slider engagement, a ball and socket engagement or hinge and hinge engagement.

20. The system of claim 13, wherein said fixing clamp and the link are fixed by a third engaging member with a predetermined angle therebetween, the hip joint installation unit and the link are relatively rotatable with respect to the first engaging member.

21. The system of claim 20, wherein said third engaging member comprises a ball and slider engagement, a slider and slider engagement, a ball and socket engagement or hinge and hinge engagement.

22. A robot mounting apparatus, comprising:

a fixing clamp comprising a bar having a predetermined length and positioned substantially perpendicular to a longitudinal direction of a femur; and a clamp end having a predetermined shape to seize the femur;

a hip joint installation unit having a predetermined shape, a hip joint operation robot installed on the hip joint installation unit, wherein the hip joint installation unit is positioned near an end portion of the femur; and a link having a predetermined length connecting the hip joint installation unit and the bar, wherein the link is positioned substantially parallel with respect to the longitudinal direction of the femur and the link is fixed by engaging the link with each of the hip joint installation unit and the bar, wherein the robot mounting apparatus is capable of being positioned near an end portion of the femur in the side of the hip joint and adapted to engage at various angles such that the hip joint operation robot operates on the femur for hip implant surgery, further wherein the hip joint operation robot is capable of forming a femoral canal cavity in the femur that matches a size of an artificial hip joint stem.

23. The robot mounting apparatus of claim 22, wherein the fixing clamp is a Roman clamp.

24. A hip joint operation robot system, comprising:

a robot that performs an artificial joint operation with respect to a femur;

a robot mounting apparatus according to claim 22; and a computer electrically connected with the robot for controlling the robot to perform the artificial joint operation.

* * * * *

UNITED STATES PATENT AND TRADEMARK OFFICE
CERTIFICATE OF CORRECTION

PATENT NO. : 7,104,998 B2  Page 1 of 1
APPLICATION NO. : 10/178726
DATED : September 12, 2006
INVENTOR(S) : Yong San Yoon et al.

It is certified that error appears in the above-identified patent and that said Letters Patent is hereby corrected as shown below:

On the Title page: under Inventors: KWON, Dong Su

Delete "Su" and replace with --Soo--

Signed and Sealed this

Twenty-seventh Day of March, 2007

JON W. DUDAS
*Director of the United States Patent and Trademark Office*